(12) United States Patent
Martin et al.

(10) Patent No.: US 6,332,776 B1
(45) Date of Patent: Dec. 25, 2001

(54) LIGHTED DENTAL PROP

(76) Inventors: Daniel H. Martin; Todd E. Davis, both of 3155 E. Patrick La., Suite 14, Las Vegas, NV (US) 89120

( * ) Notice: Subject to any disclaimer, the term of this patent is extended or adjusted under 35 U.S.C. 154(b) by 0 days.

(21) Appl. No.: 09/394,412

(22) Filed: Sep. 13, 1999

Related U.S. Application Data

(63) Continuation-in-part of application No. 09/037,682, filed on Mar. 10, 1998, now abandoned.

(51) Int. Cl.[7] .............................. A61C 5/00; A61C 1/00; A61B 1/24
(52) U.S. Cl. .............................. 433/140; 433/30; 433/29
(58) Field of Search .............................. 433/140, 30, 29; 60/199, 238, 241

(56) References Cited

U.S. PATENT DOCUMENTS

| | | | |
|---|---|---|---|
| 4,589,846 | * 5/1986 | Annoni | 433/30 |
| 4,802,851 | * 2/1989 | Rhoades | 433/93 |
| 5,429,120 | * 7/1995 | Lewitus | 600/191 |
| 5,636,984 | * 6/1997 | Gomes | 433/30 |

* cited by examiner

Primary Examiner—John J. Wilson
Assistant Examiner—Robyn Kieu Doan

(57) ABSTRACT

A lighted dental prop is disclosed comprising a wedge shaped bite block and a light source. The bite block utilizes reflected fiberoptic light or an internal light source to provide broad illumination to the mouth.

14 Claims, 7 Drawing Sheets

LIGHTED DENTAL PROP

CROSS REFERENCE TO RELATED APPLICATIONS

This application is a continuation-in-part of application ser. No. 09/037,682, filed on Mar. 10, 1998, now abandoned.

BACKGROUND OF THE INVENTION

1. Field of the Invention

In common use in the dental profession are dental props for holding the mouth open during dental procedures. Such devices are sometimes wedge shaped, and are placed near the back of the mouth, between the upper and lower teeth, opposite the side of the mouth which needs to be accessed by the practitioner. Some of these devices are replaced after each use, because of the risk of cross contamination between patients.

Also in widespread use in the dental profession are overhead lights which the practitioner must continually attempt to position in such a way that he or she does not come between the light and the patient, blocking the light from its intended target. Various devices have incorporated a light source in attempts to overcome this problem.

The present invention relates to the incorporation of a light source into a dental prop.

2. Description of the Prior Art

U.S. Pat. Nos. 4,167,814; 5,009,595; 5,205,733; and 5,588,836 are examples of dental devices which incorporate wedge shaped dental props similar to that of the present invention. None of these patents seek to provide a light to the mouth.

As shown in U.S. Pat. Nos. 2,182,390; 4,802,851; 4,991,566; 5,152,686; 5,429,120; and 5,462,435; dental devices which incorporate a light source are commonly constructed of several distinct components which must be manufactured separately, and then assembled by hand. The labor required is likely to result in a retail price which makes it unlikely that such devices will be discarded after use with one patient. Further, the design of many such devices requires a size which fills a significant portion of the mouth, and therefore leaves less maneuvering room available to the dental practitioner.

BRIEF SUMMARY OF THE INVENTION

The present invention provides for a wedge shaped dental prop for holding the dental patient's mouth open during dental procedures, which incorporates a light source. This dental prop is designed to be inserted between the patient's upper and lower teeth, on the side of the mouth opposite that which requires a dental procedure.

One embodiment utilizes a dental prop, preferably with a metallic silver coating on one side that reflects fiberoptic light to illuminate the mouth. A second embodiment utilizes a dental prop with an inclined reflective surface to reflect fiberoptic light into the mouth. A third embodiment utilizes a battery and a light source to provide illumination. Still another embodiment utilizes electromagnetic induction to power a light source within the dental prop. The light from each embodiment is directed toward the opposite side of the mouth to provide illumination at the site which requires a dental procedure.

One of the advantages which is obtained with the present invention is that light is provided to the mouth by a device which is often already present to maintain the mouth in the open position. This device is small and unobtrusive so that it does not get in the way of the practitioner and the assistant as they access the mouth with various dental instruments. The device is also designed with few components and with ease of manufacture as a criterion, to provide for very low manufacturing costs. The intent is that the lighted dental prop will be sufficiently affordable that every dental practitioner will replace it after use with a single patient, therefore preventing the possibility of cross contamination between patients.

BRIEF DESCRIPTION OF THE SEVERAL VIEWS OF THE DRAWINGS

The features of the invention can now be easier understood by reference to the following detailed description thereof, taken in conjunction with the accompanying drawings; in which.

DETAILED DESCRIPTION OF THE INVENTION

Figure 1:
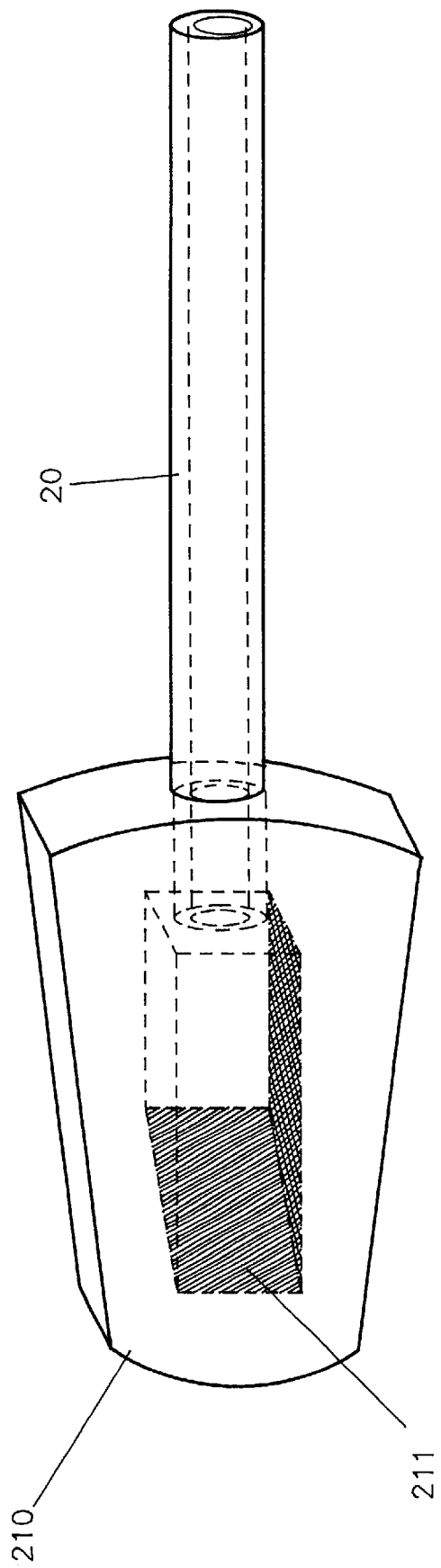
FIG. 1 is an elevation view of one embodiment of the inventive lighted dental prop assembly, incorporating an inclined surface.
Figure 2:
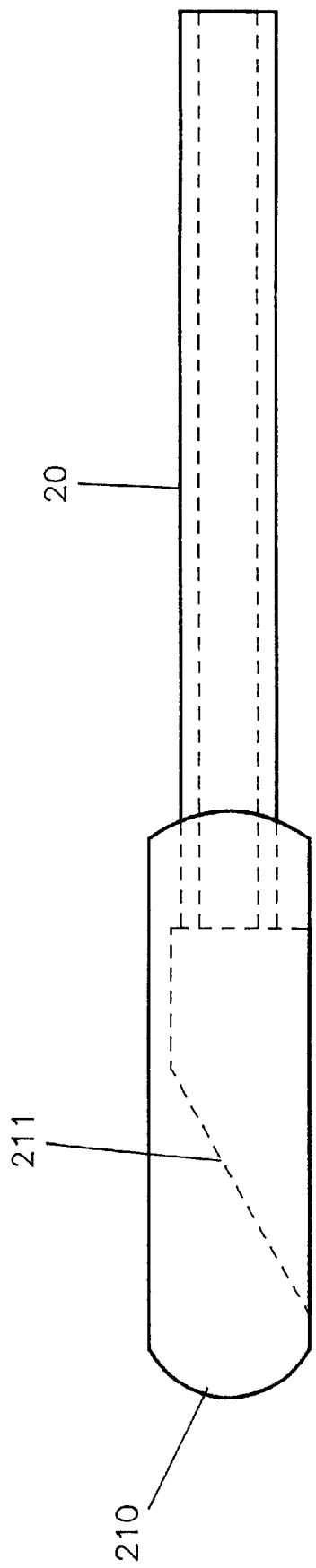
FIG. 2 is a plan view of the inventive lighted dental prop assembly.

The illustrated lighted dental prop assemblies 1, 2, 3 of the embodiments shown in FIGS. 1–5 consist of a wedge shaped bite block 10, 110, 210; to which an elongate cylindrical housing 20, 120, 220 is attached; an elongate male connector 30; a fiberoptic bundle 40; and a light source 41.

Light originates at the light source 41, is transmitted through the fiberoptic bundle 40, and is projected onto the bite block 10, 110, 210 which disburses the light to provide broad illumination to the mouth.

Figure 4:
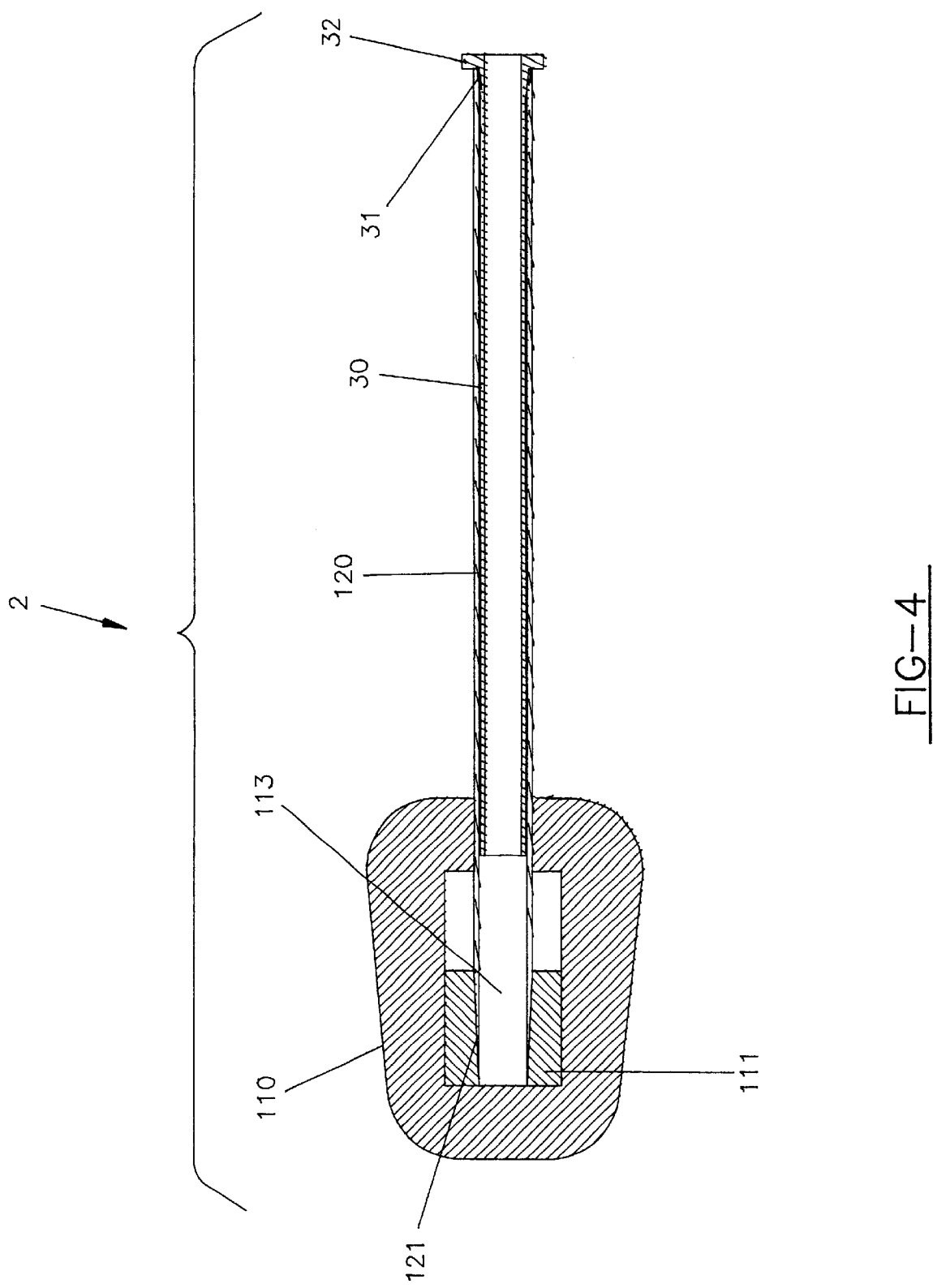
FIG. 4 is a cross-sectional view of the inventive lighted dental prop assembly, incorporating an inclined surface.
Figure 5:
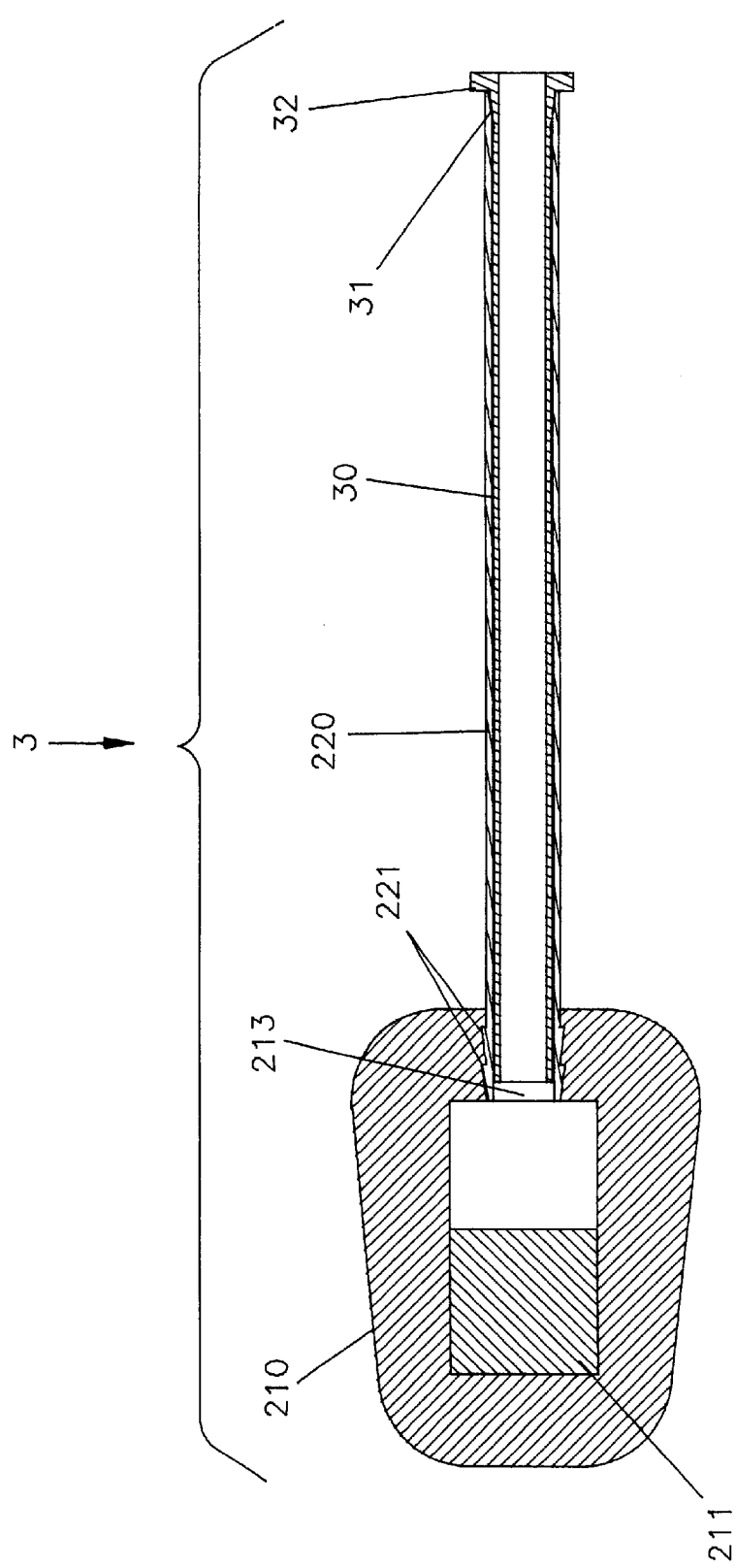
FIG. 5 is a cross-sectional view of an alternative embodiment of the inventive lighted dental prop assembly, incorporating an inclined surface.

In the embodiments portrayed in FIGS. 4–5, the light from the fiberoptic bundle 40 is projected onto an inclined portion 111, 211 of the bite block 110, 210, which acts similar to a mirror and helps to direct the disbursed light toward the teeth on the opposite side of the mouth.

Figure 3:
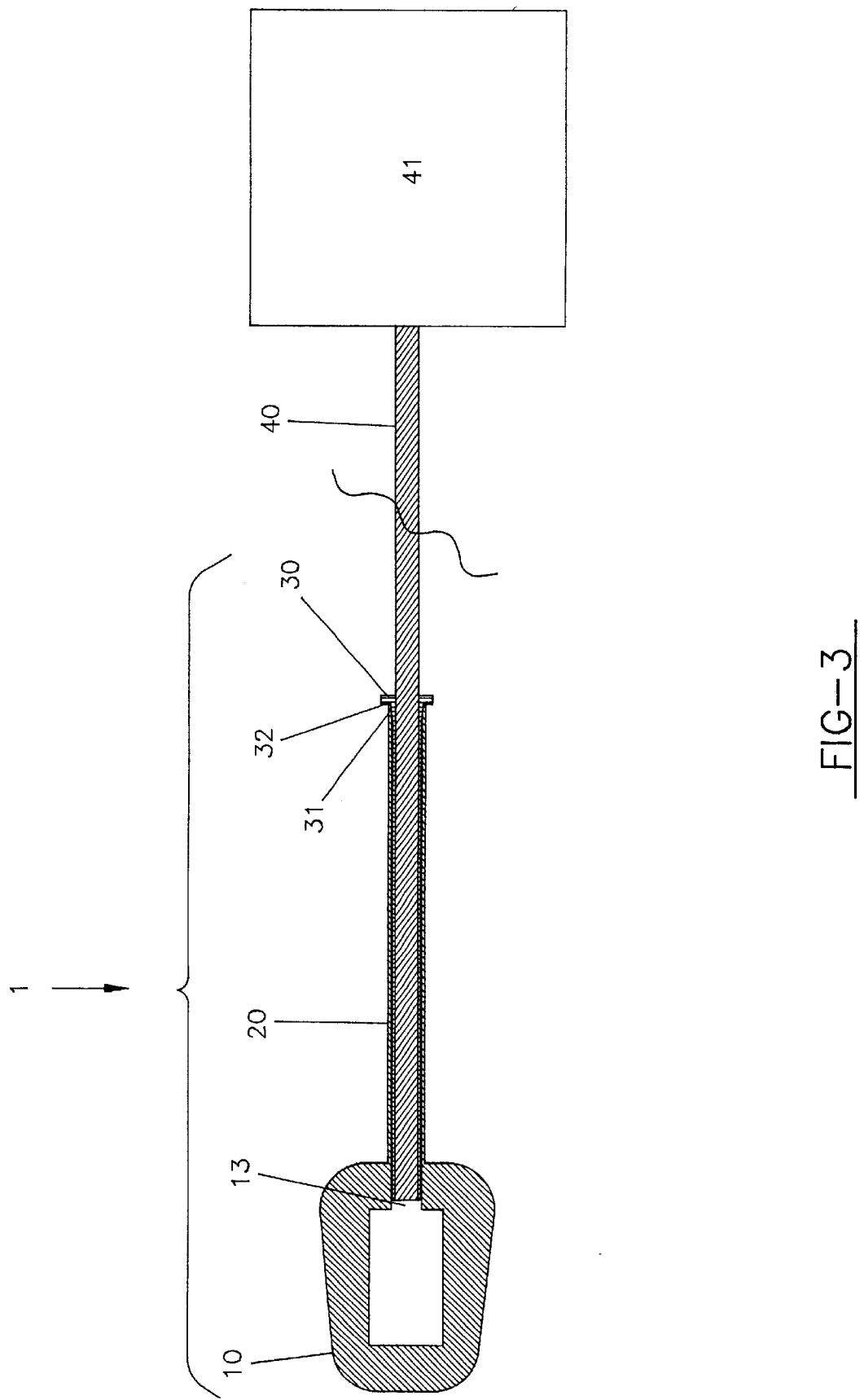
FIG. 3 is a sectional view of the inventive lighted dental prop assembly, incorporating light from a fiberoptic bundle.

In the embodiment portrayed in FIG. 3, the elongate cylindrical housing 20 is an integral portion of the bite block 10.

In the embodiment portrayed in FIG. 4, the cylindrical housing 120 is constructed with a male taper 121 at the distal end, and press fit into a cavity 113 within the bite block 110.

In the embodiment portrayed in FIG. 5, the cylindrical housing 220 is constructed with one or more barbs 221 at the distal end, and pressed into a cavity 213 within the bite block 210.

The bite block 10, 110, 210 and cylindrical housing 20, 120, 220 are designed to be disposable to prevent cross contamination. The fiberoptic bundle 40 and male connector 30 are designed to be covered by the disposable components when used with the patient.

The elongate male connector 30 is constructed with a male taper 31 at the proximal end which is press fit into the cylindrical housing 20, 120, 220 for retention. At the proximal end of the taper 31, the connector 30 is constructed with a shoulder 32 which prevents it from being accidentally pressed further than desired into the cylindrical housing 20, 120, 220.

Figure 6:
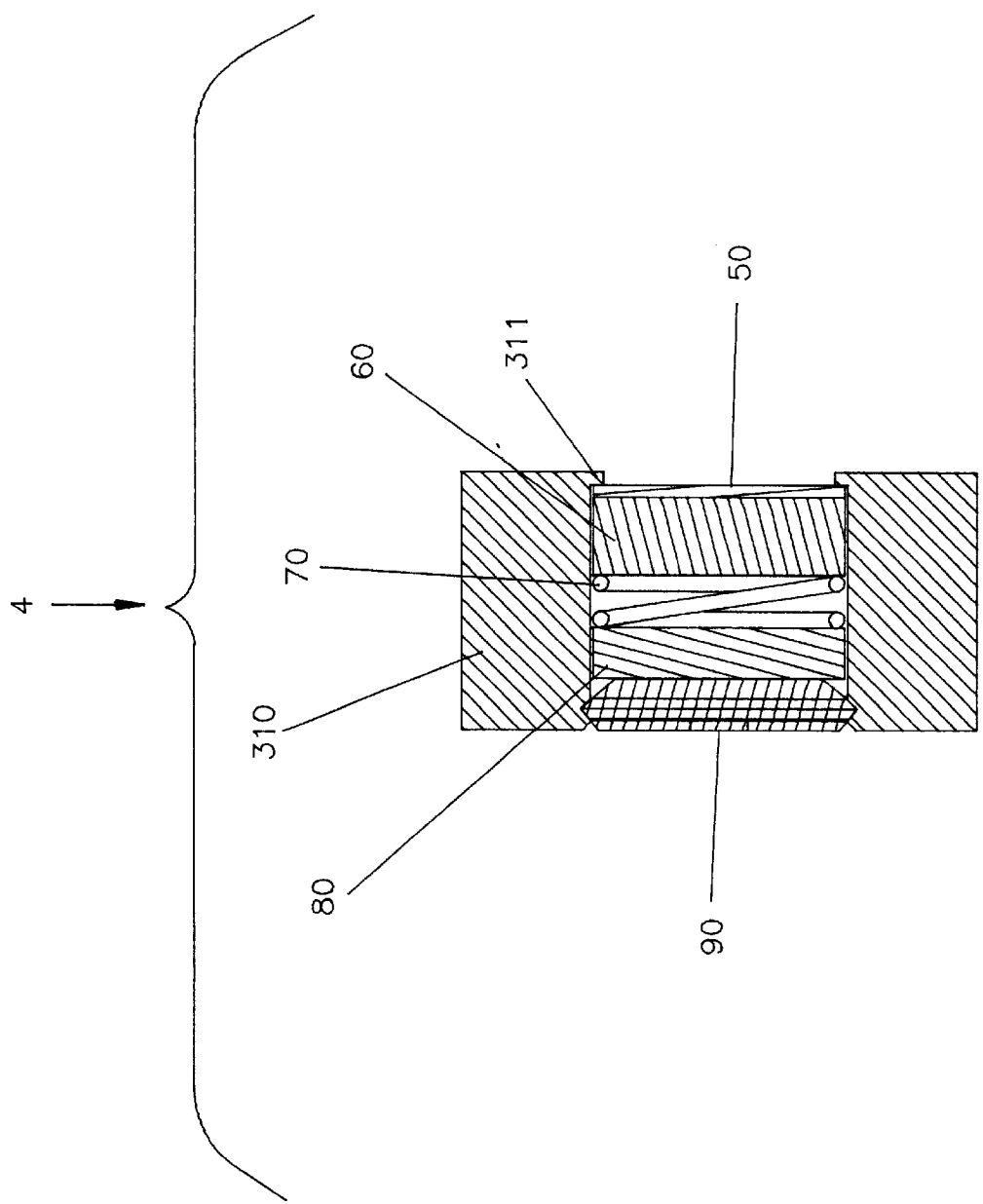
FIG. 6 is a cross-sectional view of the inventive lighted dental prop assembly, incorporating a battery and light bulb.

In the embodiment portrayed in FIG. 6, the light originates from an internal light source 60 powered from an internal battery 80. A transparent or translucent panel 50 is utilized at the surface of the bite block 310, in front of the light source 60 to prevent flesh from contacting the light source 60. A shoulder 311 and a set screw 90 are utilized to retain the internal components 50, 60, 70, 80 within the bite block 310. Just before the lighted mouth prop 4 is used with a patient, the set screw 90 is utilized to tighten a spring 70, bringing the battery 80 into contact with the light source 60 to illuminate at least the teeth on the opposite side of the mouth.

Figure 7:
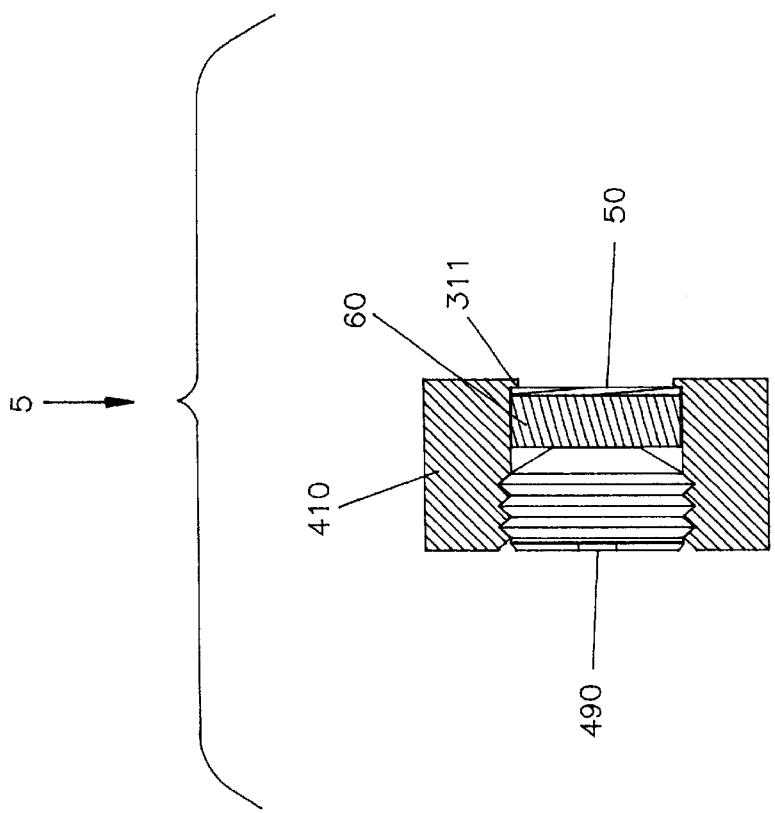
FIG. 7 is a cross-sectional view of the inventive dental prop assembly, incorporating electromagnetic induction to power a light bulb.

The embodiment portrayed in FIG. 7 utilizes electromagnetic induction. A primary induction coil 500 is placed outside the mouth in proximity to the bite block 410. The dental prop incorporates a secondary induction coil 490 to provide electricity to an internal light source 60. A transparent or translucent panel 50 is utilized at the surface of the prop 410, in front of the light source 60 to prevent flesh from contacting the light source 60. A shoulder 311 and exterior threads on the secondary induction coil 490 are utilized to retain the internal components 50, 60 within the mouth prop 410. Power is connected to the primary induction coil 500 so that electromagnetic energy is conducted between the primary 500 and secondary 490 induction coils, whereupon the secondary induction coil provides electricity to the light source 60 to illuminate the mouth. The primary induction coil 500 and power source are located outside the mouth so that there is no risk of shock to the patient or practitioner, and also to minimize the risk of cross-contamination between patients.

References herein to the details of the illustrations are by way of example only and not intended to limit the scope of the claims which themselves recite those details regarded as important to the invention.

What is claimed is:

1. A dental prop assembly comprising:
   a) a unitary body constructed such that when said body is placed between the upper and lower teeth of a patient, the mouth is held open;
   b) said unitary body formed with a first cavity on one side and second cavity on one end, said first cavity constructed with an inclined reflective surface such that the portion of the incline furthest from the second cavity is less shallow than the portion of the incline nearest the second cavity;
   c) a light source;
   d) a light conducting cable connected to said light source, whereby when said light conducting cable is attached to the second cavity, light will be reflected from the reflective surface of the first cavity and be emitted from the unitary body to illuminate the mouth of the patient.

2. The dental prop assembly of claim 1 wherein the unitary body is partially or completely constructed of a material which will allow light to pass through at least a portion of the unitary body.

3. The dental prop assembly of claim 1 further comprising an elongate cylindrical housing attached to the second cavity, whereby when the light conducting cable is inserted into the cylindrical housing, light will be emitted from the unitary body to illuminate the mouth of the patient.

4. The dental prop assembly of claim 3 wherein said cylindrical housing is constructed integrally with the unitary body.

5. The dental prop assembly of claim 3 further comprising connection means for attaching the cylindrical housing to the unitary body.

6. The dental prop assembly of claim 5, wherein said connection means comprises; the distal end of the cylindrical housing is constructed such that interference is created when the cylindrical housing is pressed into the second cavity.

7. The dental prop assembly of claim 6 wherein the distal end of the cylindrical housing is tapered.

8. The dental prop assembly of claim 6 wherein the distal end of the cylindrical housing is constructed with at least one barb.

9. The dental prop assembly of claim 1, further comprising connection means for attaching the light conducting cable to the unitary body.

10. The dental prop assembly of claim 9, wherein said connection means comprises a male connector attached to the distal end of the light conducting cable constructed such that interference is created when the male connector is pressed into the second cavity.

11. The dental prop assembly of claim 9 further comprising an elongate cylindrical housing attached to the unitary body, wherein said connection means comprises a male connector attached to the distal end of the light conducting cable constructed such that interference is created when the male connector is pressed into the cylindrical housing.

12. The dental prop assembly of claim 11 wherein said male connector is constructed with a tapered wall.

13. The dental prop assembly of claim 11 wherein said male connector is constructed with an annular protrusion, whereby the male connector is pressed into the cylindrical housing until the annular protrusion touches the proximal end of the cylindrical housing.

14. A dental prop comprising a bite block constructed with a cavity, a light source within the bite block cavity; a secondary induction coil within the bite block cavity; and retention means to retain the light source and secondary induction coil within the bite block cavity; whereby when a primary induction coil connected to a power source is placed in proximity to the dental prop, electromagnetic energy is conducted from the primary induction coil to the secondary induction coil, and the secondary induction coil provides electricity to the light source to illuminate the mouth of the patient.

* * * * *